US008128632B2

(12) United States Patent  (10) Patent No.: US 8,128,632 B2
Paris et al.  (45) Date of Patent: Mar. 6, 2012

(54) DELIVERY OF MULTICOMPONENT COMPOSITIONS

(75) Inventors: Michael W. Paris, Lansdale, PA (US); Charanpreet S. Bagga, Phoenixville, PA (US); Maarten Persenaire, Phoenixville, PA (US); Erik M. Erbe, Berwyn, PA (US)

(73) Assignee: Orthovita, Inc., Malvern, PA (US)

( * ) Notice: Subject to any disclaimer, the term of this patent is extended or adjusted under 35 U.S.C. 154(b) by 72 days.

(21) Appl. No.: 12/301,655

(22) PCT Filed: May 22, 2007
(Under 37 CFR 1.47)

(86) PCT No.: PCT/US2007/012116
§ 371 (c)(1),
(2), (4) Date: Apr. 16, 2009

(87) PCT Pub. No.: WO2007/139758
PCT Pub. Date: Dec. 6, 2007

(65) Prior Publication Data
US 2010/0234799 A1 Sep. 16, 2010

Related U.S. Application Data

(60) Provisional application No. 60/802,827, filed on May 22, 2006.

(51) Int. Cl.
*A61D 1/00* (2006.01)
*A61B 17/08* (2006.01)
*A61B 17/58* (2006.01)
*A61B 17/60* (2006.01)
*A61F 2/00* (2006.01)
*A61M 37/00* (2006.01)

(52) U.S. Cl. .............. 606/93; 606/213; 604/82
(58) Field of Classification Search .............. 604/82–92, 604/181, 187, 191, 211, 224, 235; 606/92–94; 222/390
See application file for complete search history.

(56) References Cited

U.S. PATENT DOCUMENTS

| 4,312,343 | A | 1/1982 | LeVeen et al. |
| 4,359,049 | A | 11/1982 | Redl |
| 4,979,942 | A | 12/1990 | Wolf et al. |
| 5,378,233 | A * | 1/1995 | Haber et al. .................... 604/83 |
| 5,454,793 | A | 10/1995 | Levander et al. |
| 5,468,245 | A | 11/1995 | Vargas, III |
| 5,681,872 | A | 10/1997 | Erbe |
| 5,914,356 | A | 6/1999 | Erbe |
| 6,048,346 | A | 4/2000 | Reiley et al. |
| 6,132,396 | A | 10/2000 | Antanavich et al. |
| 6,234,795 | B1 | 5/2001 | Fischer |
| 6,241,734 | B1 | 6/2001 | Scribner et al. |

(Continued)

FOREIGN PATENT DOCUMENTS

EP  1 074 231 B1  4/2003

(Continued)

OTHER PUBLICATIONS

International Search Report mailed by the EPO on Dec. 9, 2008.

*Primary Examiner* — Matthew F Desanto
(74) *Attorney, Agent, or Firm* — Stradley Ronon Stevens & Young, LLP

(57) ABSTRACT

The invention relates to devices and kits for the controlled delivery of viscous, multi component compositions.

29 Claims, 7 Drawing Sheets

U.S. PATENT DOCUMENTS

| | | |
|---|---|---|
| 6,348,055 B1 | 2/2002 | Preissman |
| 6,375,659 B1 | 4/2002 | Erbe et al. |
| 6,383,190 B1 * | 5/2002 | Preissman .................. 606/94 |
| 6,488,180 B1 | 12/2002 | Bayat |
| 6,488,649 B1 | 12/2002 | Lichten |
| 6,565,539 B1 * | 5/2003 | Zinger et al. .................. 604/191 |
| 6,572,256 B2 | 6/2003 | Seaton et al. |
| 6,575,919 B1 | 6/2003 | Reiley et al. |
| 6,582,439 B1 | 6/2003 | Sproul |
| 6,613,018 B2 | 9/2003 | Bagga et al. |
| 6,613,054 B2 | 9/2003 | Scribner et al. |
| 6,641,587 B2 | 11/2003 | Scribner et al. |
| 6,645,213 B2 | 11/2003 | Sand et al. |
| 6,676,664 B1 | 1/2004 | Al-Assir |
| 6,698,622 B2 | 3/2004 | Sawhney et al. |
| 6,712,794 B2 | 3/2004 | Kust et al. |
| 6,719,761 B1 | 4/2004 | Reiley |
| 6,749,595 B1 | 6/2004 | Murphy |
| 6,793,660 B2 | 9/2004 | Kerr et al. |
| 6,800,245 B1 | 10/2004 | Erbe et al. |
| 6,814,736 B2 | 11/2004 | Reiley et al. |
| 6,916,308 B2 * | 7/2005 | Dixon et al. .................. 604/122 |
| 7,008,433 B2 | 3/2006 | Voellmicke et al. |
| 7,029,163 B2 | 4/2006 | Barker et al. |
| 2001/0034527 A1 | 10/2001 | Scribner et al. |
| 2002/0099385 A1 | 7/2002 | Ralph et al. |
| 2003/0069545 A1 | 4/2003 | Arm |
| 2003/0130664 A1 | 7/2003 | Boucher et al. |
| 2003/0191414 A1 | 10/2003 | Reiley |
| 2004/0010260 A1 | 1/2004 | Scribner et al. |
| 2004/0024409 A1 | 2/2004 | Sand et al. |
| 2004/0049203 A1 | 3/2004 | Scribner et al. |
| 2004/0196735 A1 | 10/2004 | Barker et al. |
| 2005/0251149 A1 | 11/2005 | Wenz |
| 2007/0072146 A1 * | 3/2007 | Pierson .................. 433/90 |
| 2008/0243130 A1 | 10/2008 | Paris et al. |

FOREIGN PATENT DOCUMENTS

| | | |
|---|---|---|
| FR | 2 690 332 A1 | 10/1993 |
| WO | WO 99/49819 A1 | 10/1999 |
| WO | WO 2006/079106 A2 | 7/2006 |
| WO | WO 2007/036815 A2 | 4/2007 |
| WO | WO 2007/036815 A3 | 4/2007 |
| WO | WO 2008/121775 A2 | 10/2008 |

* cited by examiner

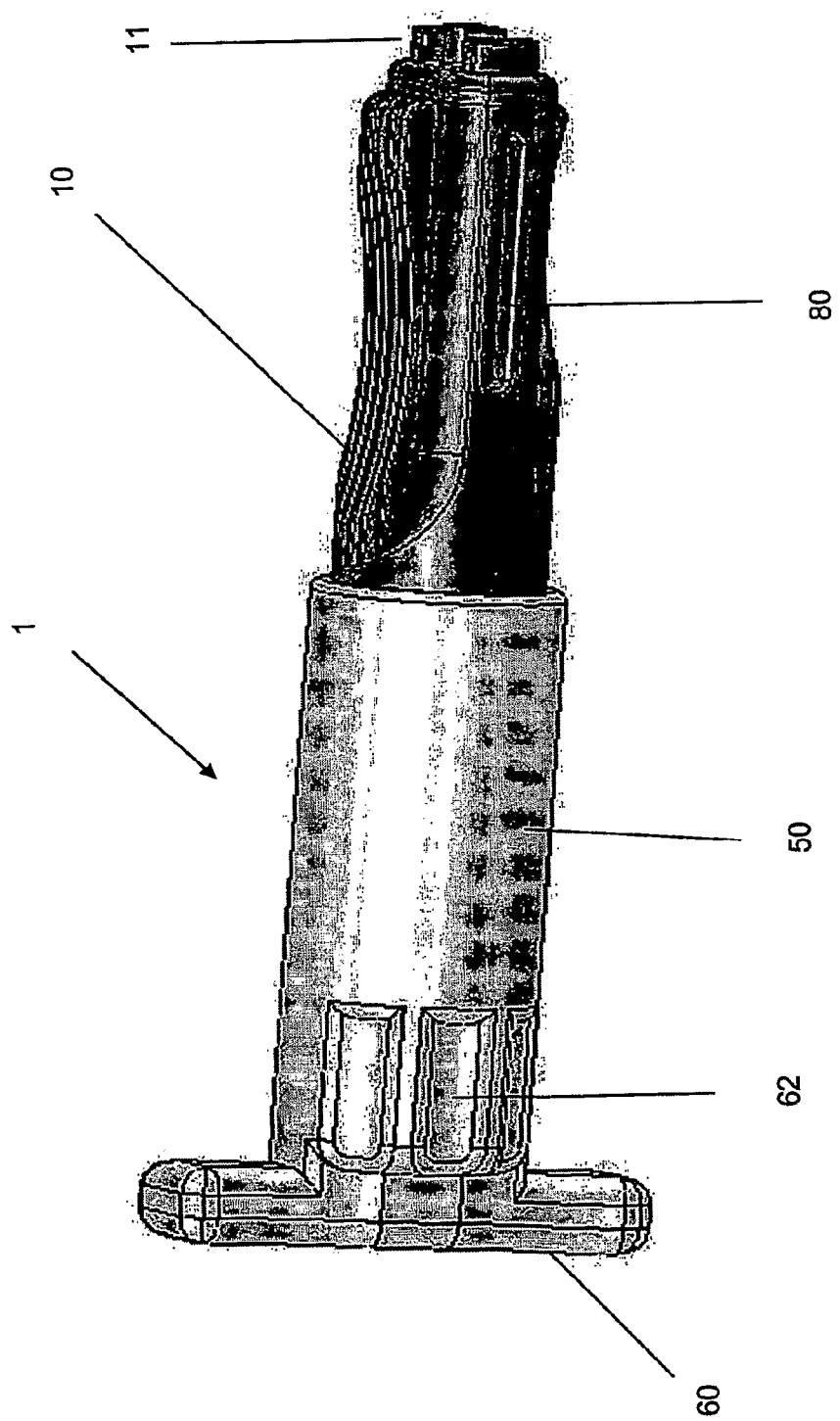

DELIVERY OF MULTICOMPONENT COMPOSITIONS

CROSS-REFERENCE TO RELATED APPLICATIONS

This application is the National Stage of International Application No. PCT/US20070/012116, filed May 22, 2007, which claims the benefit of U.S. Provisional Application No. 60/802,827 filed May 22, 2006, the disclosure of which is incorporated herein by reference in its entirety.

FIELD OF THE INVENTION

The invention relates to devices and kits for the controlled delivery of highly viscous, multi-component compositions.

BACKGROUND OF THE INVENTION

The preparation of polymerizable multi-component compositions, such as those used in orthopaedic and dental applications, is typically a two-step process. First, individual components are thoroughly mixed, for example, by stirring or simultaneous expression through a mixing device. After mixing, the resulting composition is loaded into a system for delivery of the material to the desired location. These compositions include, for example, poly (methylmethacrylate)-based compositions, as well as compositions of the type described in U.S. Pat. Nos. 5,681,872 and 5,914,356, assigned to the assignee of the present application and incorporated herein by reference in their entireties.

For some polymerizable compositions, the individual components are viscous pastes. Upon mixing, the viscosity of the resulting composition increases as the material polymerizes and sets. Working time—the amount of time before the composition becomes too viscous or rigid to be manipulated—is generally about five to eight minutes, depending on the composition. As such, the user must work expeditiously to quickly mix the components, load the composition into the delivery system, and deliver the composition to the situs, before the working time expires. Moreover, and especially in procedures where the composition is delivered within intraosseous spaces, the delivery of the composition must be extensively supervised; if the composition leaks out of the situs, numerous complications, including death, can result. Some of the working time is thus sacrificed to order to ensure the safe delivery of the compositions. Methods, devices, and kits have been developed to facilitate the mixing of the individual components, e.g., U.S. Pat. Nos. 6,375,659, 6,800,245, and 6,613,018, all assigned to the assignee of the present application and incorporated herein by reference, in their entireties.

In addition, the highly viscous quality of these materials complicates delivery as high pressures are required to express the materials from delivery devices currently used. Current delivery devices use syringe-type devices requiring manual exertion against a plunger-type device. Manual exertion makes it difficult for the user to express controlled volumes of the compositions. Moreover, as the delivery is monitored, the user may desire to stop the expression of the composition and observe whether any seepage or leaking of the material has occurred. The highly viscous quality of the materials hinders the ability to timely stop and resume delivery.

Currently, precious minutes of working time are consumed by the mixing of the components and loading of the composition into a delivery device. Thus, there is a need for devices that minimize the time between the mixing of the components and the delivery of the compositions to the situs. Additionally, there remains a need to deliver these highly viscous compositions with greater control.

SUMMARY OF THE INVENTION

The present invention relates to devices for the delivery of multi-component composite materials comprising a barrel having a first and second chamber for holding the components, the chambers being aligned along a longitudinal axis of the barrel; a plunger comprising first and second distal legs adapted for slidable entry into the chambers of the barrel and having a proximal end of the plunger comprising external threads; and a plunger actuation member having internal threads for cooperation with the external threads of the plunger such that rotation of the plunger actuation member slidably displaces the plunger legs into the barrel chambers. In some embodiments, rotation of the plunger actuation member advances the plunger legs into the barrel chambers.

The present invention also relates to kits for the delivery of multi-component composite materials comprising a barrel having a first and second chamber for holding the components, the chambers being aligned along a longitudinal axis of the barrel; a plunger comprising first and second distal legs adapted for slidable entry into the chambers of the barrel and having a proximal end of the plunger comprising external threads; and, a plunger actuation member having internal threads for cooperation with the external threads of the plunger such that rotation of the plunger actuation member slidably displaces the plunger legs into the barrel chambers. In some embodiments, rotation of the plunger actuation member advances the plunger legs into the barrel chambers.

The invention also relates to kits for the delivery of multi-component composite materials comprising a barrel having a first and second chamber for holding a first and second component, the chambers being aligned along a longitudinal axis of the barrel; a plunger comprising first and second distal legs adapted for slidable entry into the chambers of the barrel and having a proximal end of the plunger comprising external threads; and a plunger actuation member having internal threads for cooperation with the external threads of the plunger such that rotation of the plunger actuation member slidably displaces the plunger legs into the barrel chambers and displaces the first and second components into a mixing member to mix the two components to form a composite material. In some embodiments, rotation of the plunger actuation member advances the plunger legs into the barrel chambers and displaces the first and second components into a mixing member to mix the two components to form a composite material.

BRIEF DESCRIPTION OF THE DRAWINGS

FIG. 1 depicts one embodiment of the device of the present invention.

DETAILED DESCRIPTION OF ILLUSTRATIVE EMBODIMENTS

The devices and kits of the present invention facilitate the delivery of polymerizable multi-component compositions by obviating the step of transferring the mixed composition to a second delivery device. Moreover, the screw- or cam-type mechanism of the devices and kits of the present invention provide a mechanical advantage over conventional syringe-type devices in that the force exerted by the user translates into a higher delivery force, thereby allowing viscous materials to be delivered with less exerted force. One of skill in the art would be able to determine the torque required to maximize delivery force while minimizing exerted force. This allows for more controlled delivery of highly viscous materials.

Figure 1A:
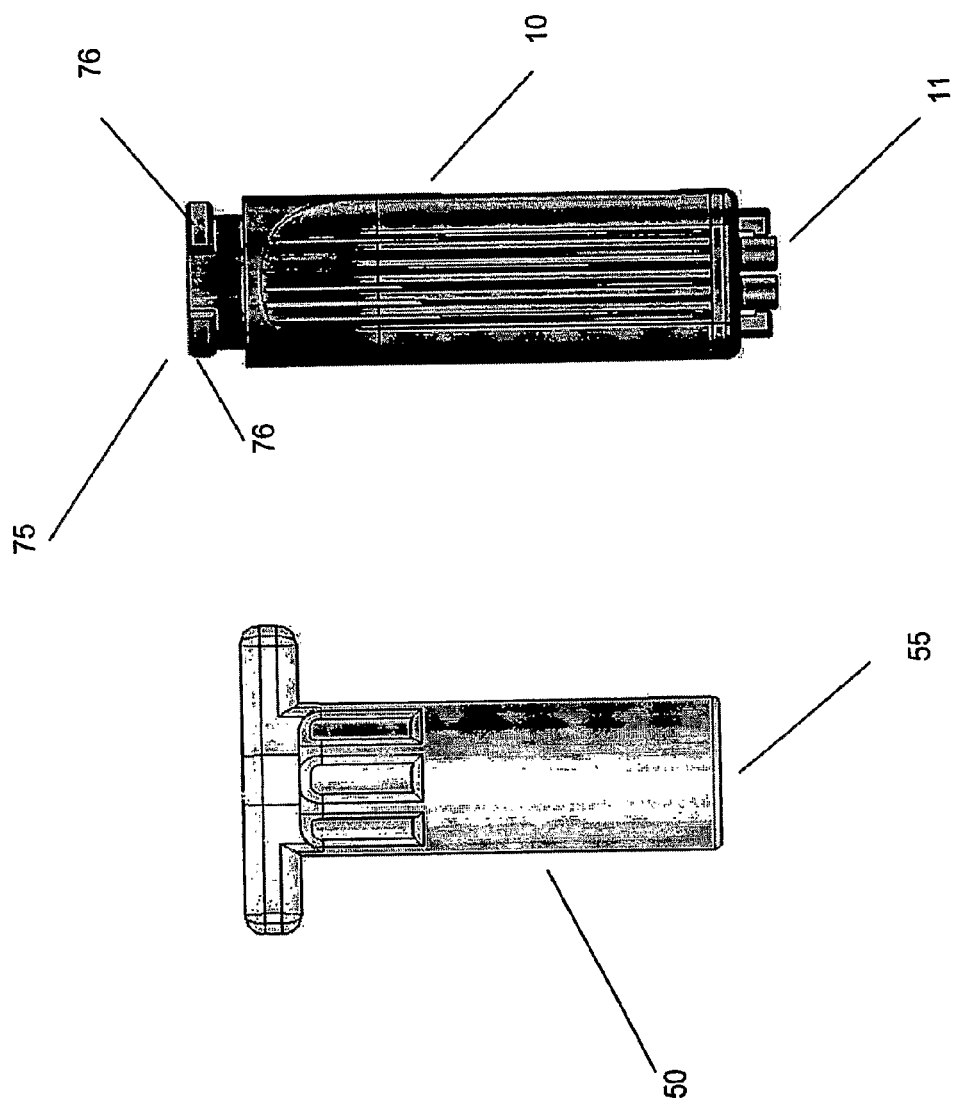
FIG. 1A depicts one embodiment of a plunger actuation member and one embodiment of a barrel of the present invention.
Figure 2:
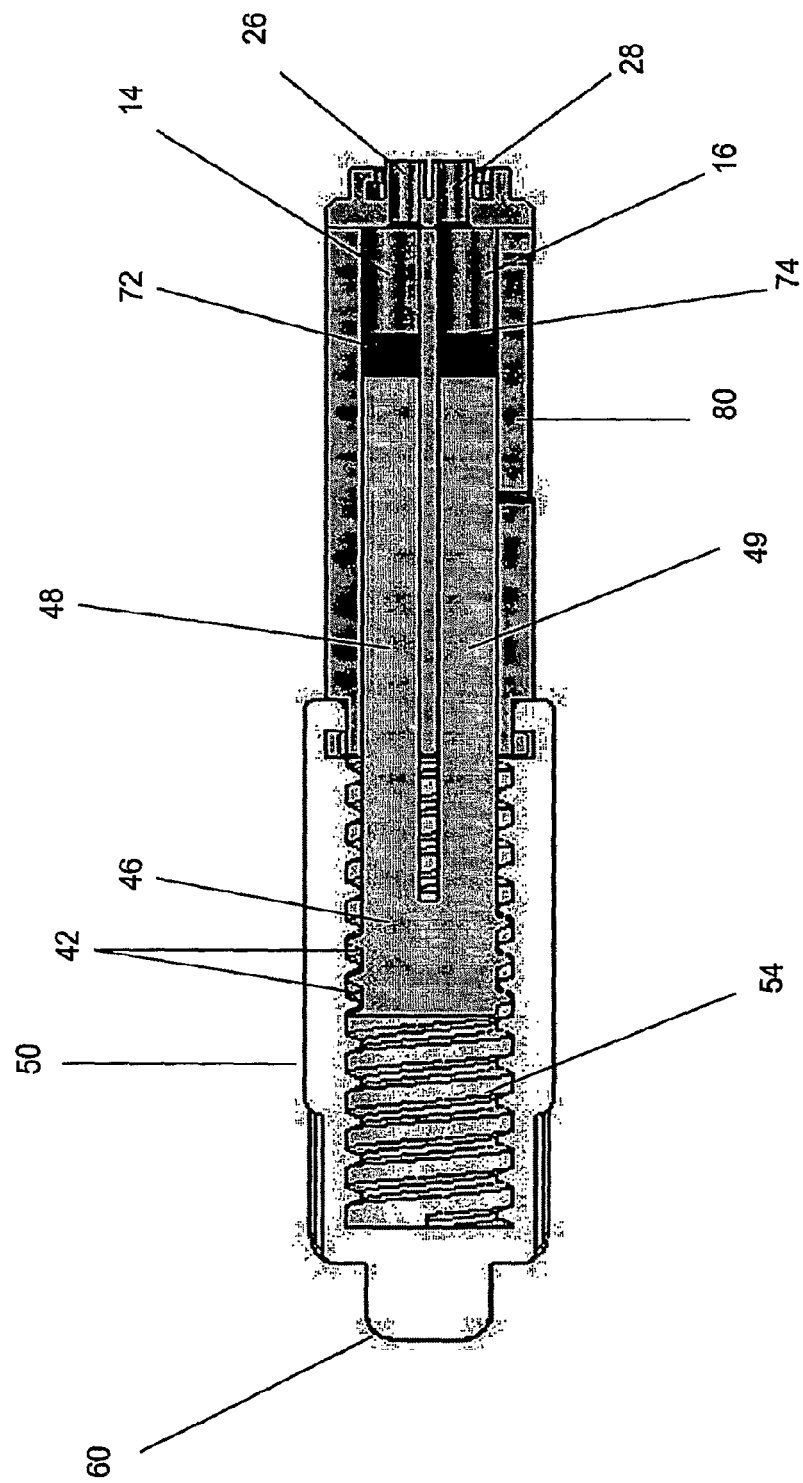
FIG. 2 depicts a longitudinal cross-section of one embodiment of a device of the present invention.
Figure 3:
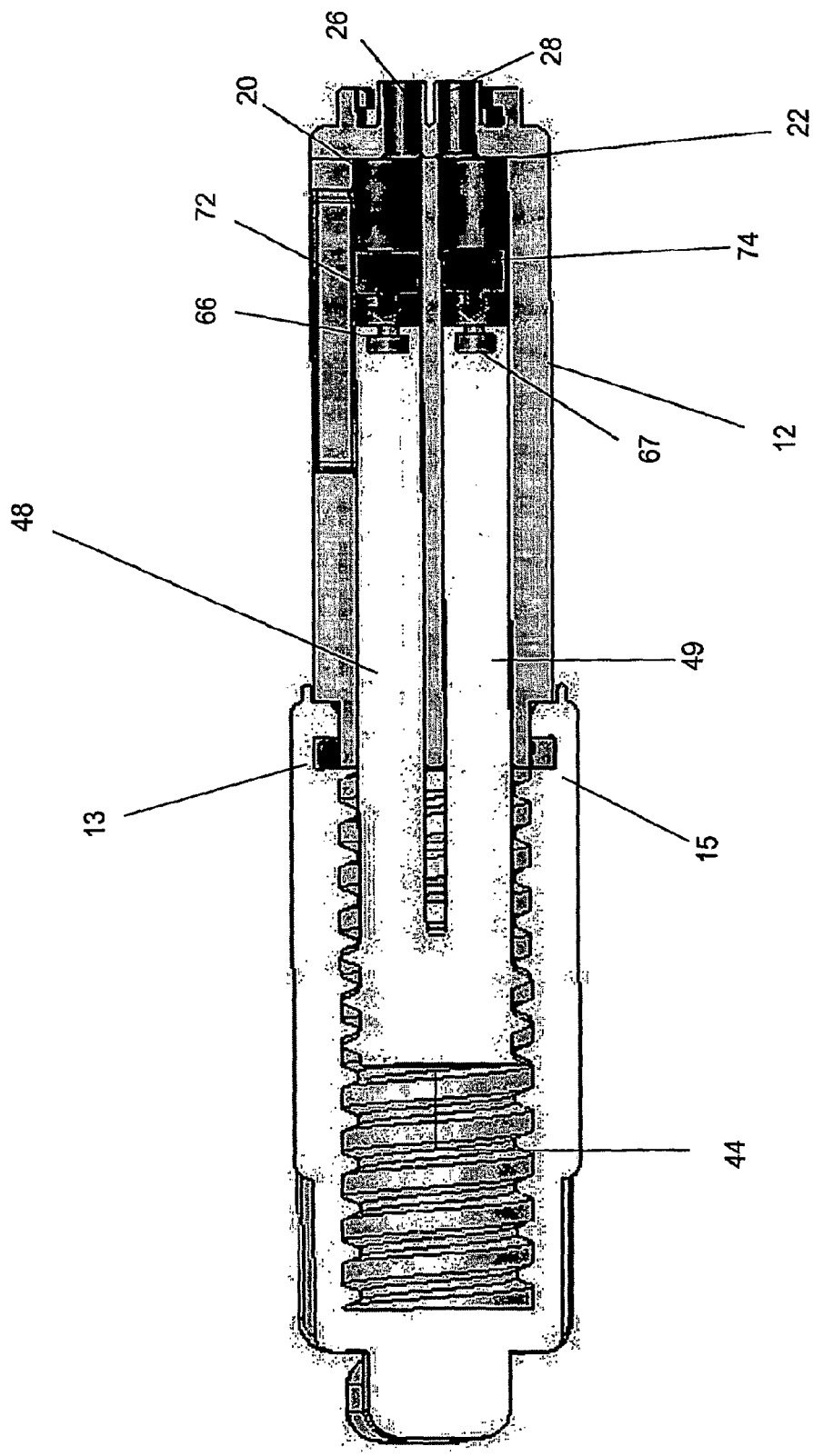
FIG. 3 depicts a longitudinal cross-section of another embodiment of a device of the present invention.
Figure 4:
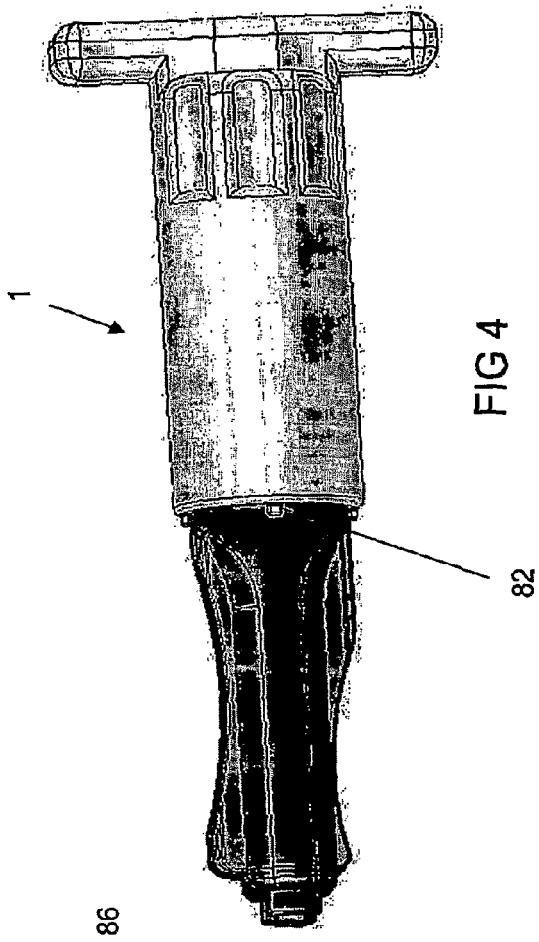
FIG. 4 depicts an embodiment of a device of the present invention comprising detents.

Turning to the figures, one embodiment of the present invention is depicted in FIGS. 1-8. As depicted in FIGS. 1-3, devices of the present invention such as 1, comprise a barrel 10 having a first (14) and second (16) chamber for holding the individual components of a polymerizable multi-component composition (not shown). In some embodiments, the barrel can comprise a single chamber, or can comprise at least two chambers for accommodating two or more substances to be expressed from the device. For example, the barrel can comprise three chambers, two chambers for separately accommodating two components of a polymerizable multi-component composition, and a third chamber for accommodating another useful agent, such as an antibiotic. The present invention does not contemplate any limitations on the possible number of chambers within the barrel or on the types of substances that can be accommodated by such chambers. When a barrel is said to contain a first and a second chamber, such expression is not intended to limit the number of possible chambers to two. In addition, where two or more chambers are present, the respective chambers may be similarly or differently volumetrically sized. Thus, for example, given a device having a barrel that includes three chambers, two chambers may have the same volumetric capacity, and the third chamber may be differently volumetrically sized. The barrel also has a distal end 11. The chambers are aligned along the longitudinal axis of the barrel. The lengths and diameters of the chambers may be determined by one of skill in the art, depending on the identity of the components and the resulting multi-component polymerizable composition. In some embodiments, the chambers are of substantially identical length and diameter. In other embodiments, the chambers may have non-identical lengths and/or diameters. The distal ends of the chambers (20, 22) further comprise ports (26, 28) extending through the wall 12 of the barrel such that the individual components may be expressed through the ports.

The devices of the present invention further comprise a plunger 44 having first (48) and second (49) distal legs that are adapted for slidable entry into the chambers of the barrel. The lengths and diameters of the legs will depend on the length and diameter of the chambers. The number of legs will depend on the number of chambers. Ideally, there will be one leg per chamber, and such leg will be appropriately sized in terms of length and diameter to "match" a corresponding chamber. In some embodiments, the lengths and diameters of the plungers may be substantially identical. In others, the legs may have non-identical lengths and/or diameters. It is envisioned that the legs would enter at the proximal ends of the chambers (13, 15) for advancement along the longitudinal axes of the chambers. In addition, the proximal end of the plunger 46 can comprise external threads 42.

In some embodiments, the plunger 44 is housed within a plunger actuation member 50. The plunger actuation member can have internal threads 54 along its longitudinal axis.

The plunger actuation member and the plunger need not be equipped with full "threads" per se, and may include any feature that permits mechanical cooperation between the plunger actuation member and the proximal end of the plunger such that rotation of the plunger actuation member advances the plunger legs into the barrel chamber. Accordingly, as used herein, the term "threads" refers to any feature that permits the described mechanical cooperation. For example, the threads may comprise a cam-type arrangement.

In some embodiments, the plunger actuation member further comprises a gripping feature 62. The gripping feature provides a surface with which the user may comfortably rotate the plunger actuation member with torque sufficient to express the individual components, as well as the composite of the multi-component polymerizable composition, during mixing and after mixing. In some embodiments, the plunger actuation member may further comprise a handle 60. The handle provides a surface with which the user may comfortably rotate the plunger actuation member with torque sufficient to express the individual components, as well as the composite of the multi-component polymerizable composition, during mixing and after mixing. In some versions of the present invention, the handle may have a generally "T"-shaped configuration.

In some embodiments of the present invention, the proximal end 75 of the barrel 10 comprises a means for attaching the barrel to the plunger actuation member. For example, attachment means may comprise a tongue and groove-type assembly wherein the proximal end of the barrel may comprise tongues 76 that can align with corresponding grooves (not shown) located at the distal end 55 of the plunger actuation member.

The internal threads 54 of the plunger actuation member are designed such that they act in cooperation with the external threads 42 of the proximal end of the plunger so that rotation of the plunger actuation member results in the movement of the plunger along the longitudinal axes of the chambers in an assembled device of the present invention. As used herein, rotation refers to the turning of either the plunger actuation member or the barrel over a predetermined arc. The internal threads 54 act in cooperation with the external threads 42 of the plunger so that rotation of the plunger actuation member 50 results in the movement of the plunger 44 and distal legs 48 and 49 along the longitudinal axes of the chambers (14, 16). In preferred embodiments, the internal threads engage the external threads of the plunger to advance the distal legs in the barrel chambers. In some embodiments, the internal and external threads are dispersed and aligned such that rotation of the plunger actuation member results in movement of the plunger and the distal legs of the plunger a pre-determined distance along the longitudinal axes. This movement along the pre-determined distance displaces a pre-determined volume of a material from within the chambers. In preferred embodiments, the material is a component of a multi-component polymerizable composition. In one embodiment, one rotation may result in about a 0.5 cc displacement of the material. In other embodiments, one rotation may result in about a 0.1 cc displacement of the material. One of skill in the art would be able to determine the placement of the threads necessary to result in a predetermined material volume displacement.

In some preferred embodiments, when the plunger actuation member is rotated, it moves in the radial direction but is substantially stationary in the longitudinal direction. In other embodiments, when the plunger actuation member is rotated, it moves in the radial direction and the longitudinal direction.

Figure 6:
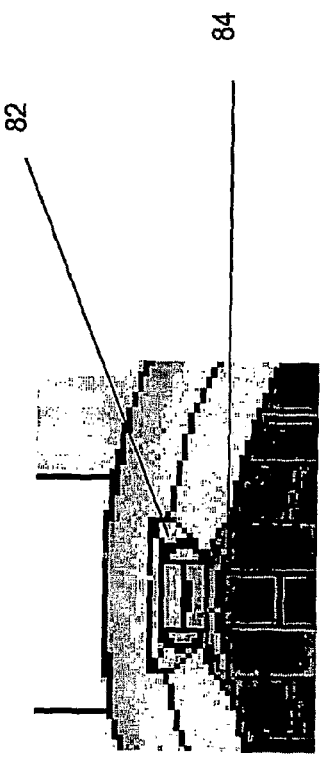
FIG. 6 depicts an enlarged view of detents of the present invention.
Figure 5:
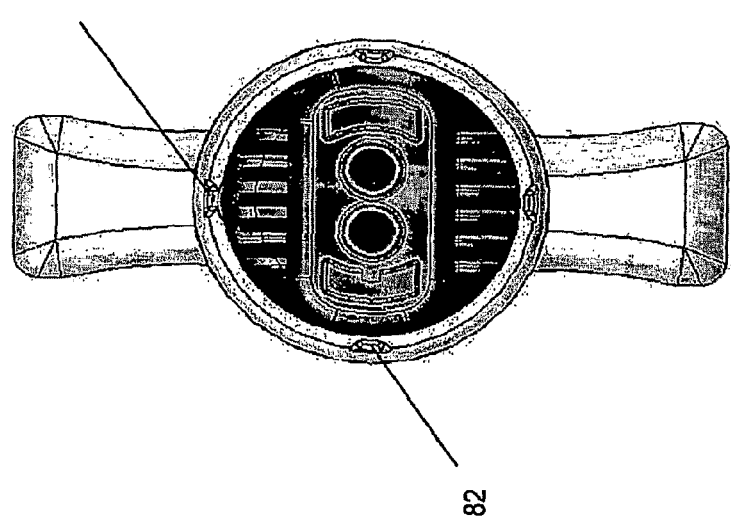
FIG. 5 depicts a downward view of one embodiment of the present invention.
Figures 7A, 7B:
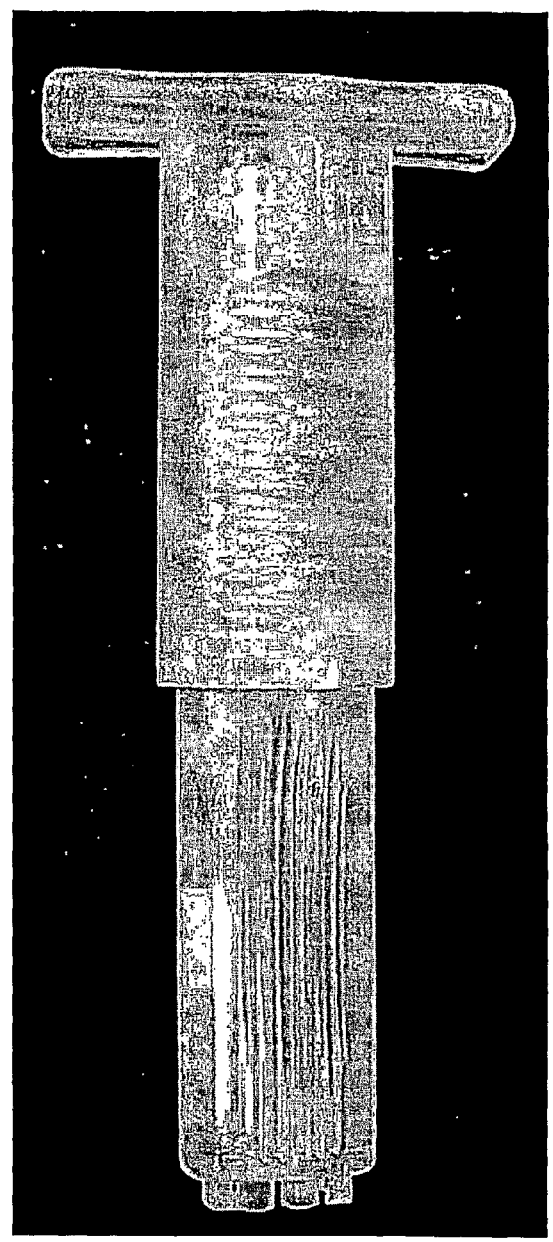
FIG. 7A depicts an embodiment of a kit of the present invention comprising a barrel, a plunger, and a plunger actuation member.
FIG. 7B depicts an assembled device of the present invention.

In certain embodiments, the devices of the present invention further comprise detents such that rotation results in an auditory and/or tactile signal to the user. The detents correspond to a specific angular rotation of the actuation member, which is calibrated to a certain volume of material displacement as presented above. The auditory and/or tactile signal therefore communicates to the user that a specific volume of material has been expressed. For example, as shown in FIGS. 5-6, in some embodiments, the distal end of the plunger actuation member (55) comprises at least one detent 82. Preferably, the plunger actuation member comprises more than one detent 82. More preferably, the plunger actuation member comprises at least four detents 82. In some embodiments, the proximal end of the barrel (75) further comprises at least one detent 84. Preferably, the barrel comprises one detent. As the user rotates the plunger actuation member, the detents 82 of the plunger actuation member contact the detent 84 of the barrel. The contact of the detents is depicted in FIG. 6 and as 86 in FIG. 5. As detent 82 passes detent 84, the user hears the contact of the two detents as an auditory signal that the detents have contacted. In some embodiments, the user feels the contact of the detents as a tactile signal that the detents have contacted.

Figure 8:
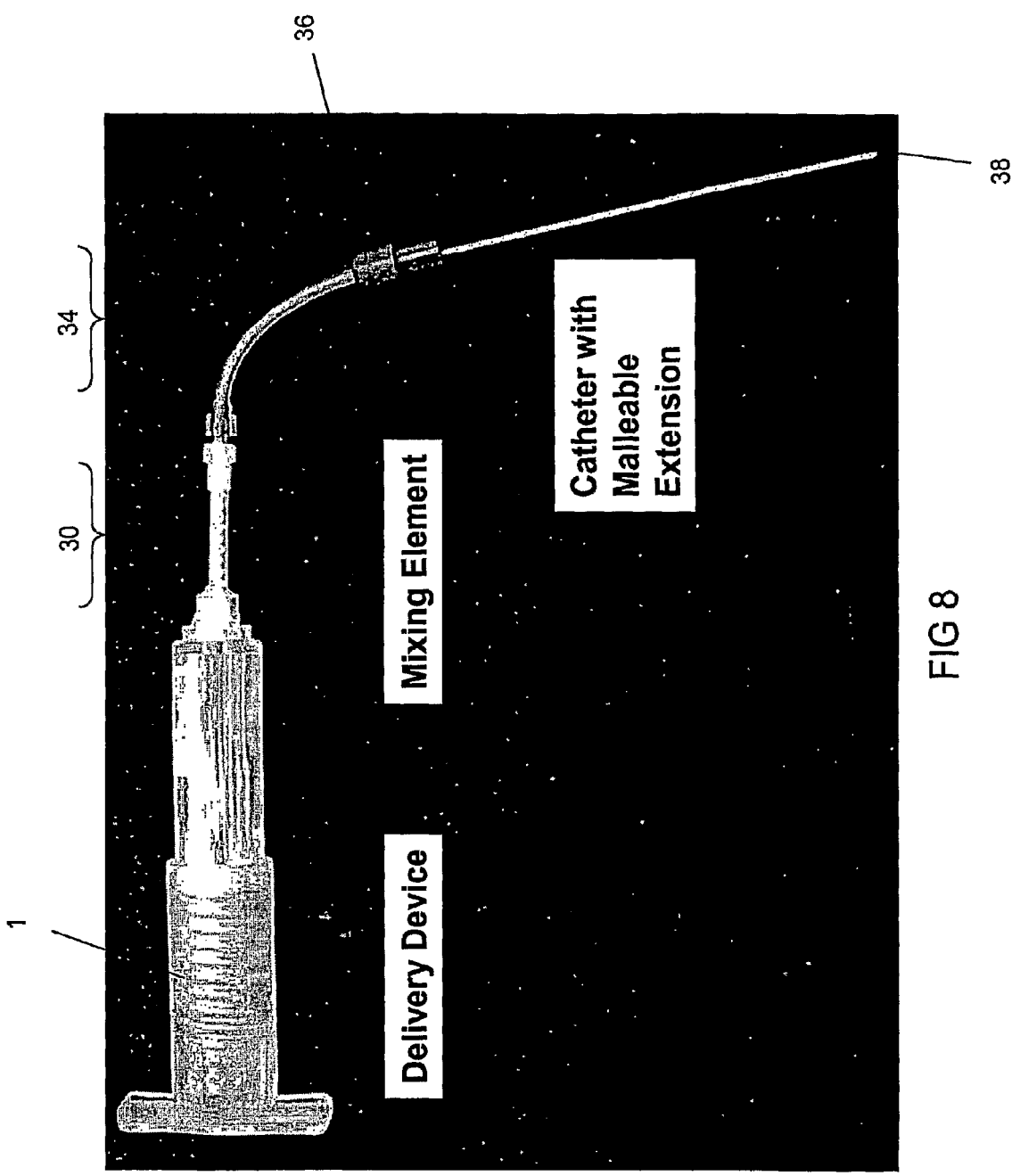
FIG. 8 depicts an embodiment of a device of the present invention.

In some embodiments of the present invention, the device further comprises a mixing element 30 for blending the components substantially homogeneously (see FIG. 8). Such mixing elements are available from MixPac Systems AG, Switzerland. Alternatively, other available mixing elements or delivery tips may be used. The distal end of the barrel 11 may further comprise a means for receiving the mixing element.

In another embodiment of the present invention, the device further comprises at least one catheter (see FIG. 8). In some applications, it may be desirable that the catheter is substantially rigid (38). In others, it may be desirable that the catheter is substantially flexible (34). In yet others, it may be desirable that the catheter comprise regions that are substantially rigid, in addition to other regions that are substantially flexible. In still others, the catheter is substantially malleable. In those embodiments wherein the device comprises two or more catheters, the catheters may be connected using an adapter such as that depicted as 36.

In certain embodiments of the present invention, the chambers may be pre-loaded with the components for the multi-component polymerizable composition. Such methods of filling the chambers with the components of a multi-component polymerizable composition are known in the art. Alternatively, the chambers may be adapted for accommodating cartridges that are loaded with the components for the multi-component polymerizable composition or with other useful agents. The barrel of the present invention may be structured to permit the insertion of a single cartridge having separate compartments that respectively contain components for the multi-component polymerizable composition or other useful agents, or the chambers may individually accept cartridges that are respectively loaded with a single component for the multi-component polymerizable composition, or with another useful agent. In some embodiments, pistons 72 and 74 (FIGS. 2 and 3) may be placed within the chambers to aid in the filling process and in the advancement of the components through the chambers. As the chambers are filled from the distal ends 20 and 22, the pistons advance to the proximal ends of the chambers (13, 15).

The user attaches the plunger actuation member, in which the plunger is housed, to the barrel using the attachment means. In some embodiments, the distal legs of the plunger further comprise means for attaching (66, 67; FIG. 3) such that upon assembly, the pistons will attach to the distal legs. In such embodiments, the pistons form a substantially airtight seal with the walls of the chamber, such that material backflow is substantially prevented. The pistons also aid in the advancement of the components through the chambers and aid in the clearing of the components from the walls of the chambers.

In certain embodiments, a mixing element is attached to the distal end of the barrel. In other embodiments, a catheter is attached to the mixing element. In others, the catheter is in series with the mixing element. The separate elements of the device are comprised of materials that are non-compliant and that can withstand the high pressures necessary to express highly viscous components and compositions. Bone cements are typically viscous, viscosity being the measure of the internal friction of the material. The greater the internal friction, the great the amount of force, or "shear," required to cause the movement of the material. When force is applied to cause movement of a viscous material contained within a closed space, internal pressures within the space result. Devices of the present invention withstand pressures of up to about 1000 psi. In other embodiments, the devices of the present invention withstand pressures of up to about 500-2000 psi.

In some embodiments, devices of the present invention may be provided as kits wherein the barrel, plunger actuation member, and plunger are provided unassembled. Such kits may further comprise mixing elements and catheters. Instructions for assembly and use of the devices may also be included.

The devices of the present invention may be used whenever a multi-component polymerizable composition is to be delivered to a situs. In some embodiments, the devices of the present invention may be used to deliver a multi-component polymerizable composition to an intraosseous situs. During the procedure, the situs may be prepared to receive the composition and the catheter 38 placed within the situs. To deliver a multi-component polymerizable composition using a device of the present invention, the device is assembled and the user rotates the plunger actuation member 50. In certain embodiments, the rotation is facilitated using the handle 60 and/or the gripping feature 62. Because the components are generally highly viscous, the ability to provide a rotating action, rather than a pushing action, facilitates the controlled actuation of plunger 44. As the plunger actuation member is rotated, the internal threads 54 cooperate with the external threads 42 to advance the distal legs 48 and 49 along the longitudinal axes of the chambers 14 and 16 that contain the components of the multi-component polymerizable composition. As the plunger actuation member is rotated and the distal legs advance into the chambers, the components will be expressed through the chambers and through ports 26 and 28. In certain embodiments, pistons 72 and 74 form a substantially airtight seal with the walls of the chamber, such that material backflow is substantially prevented. The pistons also aid in the advancement of the components through the chambers and aid in the clearing of the components from the walls of the chambers.

As the components are expressed through the ports, they advance into the mixing element 30, wherein the components are mixed substantially homogenously. Continued rotation of the plunger actuation member, continued advancement of the distal legs, and continued expression of the components from the chambers provides the force required to express the components through the device of the present invention. In a preferred embodiment of the present invention, the combined volume of the chambers, and hence the combined volume of the components, is greater than the combined volume of the mixing element, catheter, and situs.

Further rotation of the plunger actuation member causes the multi-component polymerizable composition to advance through the mixing element. In some embodiments, an indicator 80 is within the barrel 10 such that the advancement of the distal legs through the chambers may be monitored. In some embodiments, continued rotation advances the compositions into and through a catheter. In some embodiments, as the plunger actuation member is rotated, the detents 82 and 84 contact to produce an auditory and/or tactile signal to the user that a rotation has occurred. In those embodiments wherein the threads have been placed such that a rotation corresponds to a predetermined volume displacement, the auditory and/or tactile signal alerts the user that the predetermined volume has been displaced.

Continued rotation advances the composition through the catheter into the situs. Where the multi-component polymerizable composition comprises radiopaque materials, the advancement of the composition into the situs may be monitored using fluoroscopy. In some embodiments, it may be desirable that a flexible catheter 34 be employed. A flexible catheter allows the user freedom of movement and may allow the user to deliver the composition without his or her hands or arms entering the radiation field.

Retraction of the plungers by reverse rotation of the plunger actuation member releases the pressure on the material. This rotation feature of the present invention permits the user to stop the advancement of the components and composition to monitor the volume of the composition delivered within the situs. The user can also stop the advancement of the components and composition to monitor whether seepage or leaking has occurred. The user may then resume advancement through rotation of the plunger actuation member. Rotation of the plunger actuation member is facilitated by the mechanical advantage presented by the screw-type mechanism of the internal and external threads, in comparison with the push-type mechanism of a conventional syringe-type device.

Thus, there have been described presently preferred embodiments of devices and kits for the delivery of multi-component polymerizable compositions. While the present invention has been particularly shown and described with reference to the presently preferred embodiments thereof, it is understood that the invention is not limited to the embodiments specifically disclosed herein. Numerous changes and modifications may be made to the preferred embodiments of the invention, and such changes and modifications may be made without departing from the spirit of the invention. It is therefore intended that the appended claims cover all such equivalent variations as they fall within the true spirit and scope of the invention.

What is claimed:

1. A device for the delivery to a situs of multi-component, highly viscous, polymerizable, composite materials comprising:

a barrel having a first and second chamber for holding the components, the chambers being aligned along a longitudinal axis of the barrel, and at least one tongue;

a plunger comprising first and second distal legs adapted for slidable entry into the chambers of the barrel and having a proximal end of the plunger comprising external threads; and a plunger actuation member having at least one groove aligned with the at least one tongue for attaching the barrel to the plunger actuation member, a handle permitting rotation of the plunger actuation member with torque sufficient to express the components, and internal threads for cooperation with the external threads of the plunger such that rotation of the plunger actuation member advances the plunger legs into the barrel chambers, such cooperation between the internal threads of the plunger actuation member and the external threads of the plunger allowing the device to withstand pressures up to about 500 to 2,000 psi, the plunger being completely surrounded by the plunger actuation member.

2. The device of claim 1 further comprising a catheter.

3. The device of claim 2 wherein the catheter is in series with a mixing element.

4. The device of claim 3 wherein the combined volume of the chambers is greater than the combined volume of the mixing element and the catheter.

5. The device of claim 3 wherein the catheter has a substantially flexible region and a substantially rigid region connected by an adapter.

6. The device of claim 2 wherein the catheter comprises substantially rigid material.

7. The device of claim 2 wherein the catheter comprises substantially flexible material.

8. The device of claim 2 wherein the catheter comprises substantially malleable material.

9. The device of claim 2 wherein the catheter comprises both flexible and rigid regions.

10. The device of claim 1 further comprising an indicator for assessing the contents of the chambers.

11. The device of claim 10 wherein the indicator further comprises gradations.

12. The device of claim 1 further comprising a mixing element for blending the components substantially homogeneously after the components are expressed from the chambers.

13. The device of claim 1 wherein the rotation over a predetermined arc results in the displacement of the plunger legs a predetermined distance along the longitudinal axes of the chambers.

14. The device of claim 1 wherein rotation results in an auditory signal.

15. The device of claim 1 wherein rotation results in a tactile signal.

16. The device of claim 1 wherein the rotation results in a visual signal.

17. The device of claim 1 further comprising a means for visualizing the interior of the chambers.

18. The device of claim 1 wherein the distal legs further comprise distal ends adapted for receiving pistons.

19. The device of claim 1 wherein the barrel has a third chamber for holding another agent to be added to the composite material and the plunger comprises a third distal leg adapted for slidable entry into the third chamber of the barrel.

20. The device of claim 1 further comprising a first and second cartridge loaded with the components, and wherein the first and second chambers are adapted to accommodate the respective first and second cartridges.

21. A device for the delivery to a situs of multi-component, highly viscous, polymerizable, composite materials comprising:
- a barrel having a first and second chamber for holding separately respective first and second components, the chambers being aligned along a longitudinal axis of the barrel and each having a volume;
- a plunger comprising first and second distal legs adapted for slidable entry into the chambers of the barrel and having a proximal end of the plunger comprising external threads;
- a plunger actuation member having a handle permitting rotation of the plunger actuation member with torque sufficient to express the first and second components and internal threads for cooperation with the external threads of the plunger such that rotation of the plunger actuation member advances the plunger legs into the barrel chambers and displaces the first and second components from the barrel chambers, the plunger being completely surrounded by the plunger actuation member; and
- an attachment mechanism between the barrel and the plunger actuation member, the mechanism further allowing the device to withstand pressures up to about 500 to 2,000 psi; a mixing element for receiving the components from the barrel chambers and blending the components substantially homogeneously to form the composite material, the mixing element having a volume; and
- a catheter having a volume and delivering the composite material to the situs, wherein the combined volume of the chambers is greater than the combined volume of the mixing element and the catheter.

22. The device of claim 21 wherein the rotation over a predetermined arc results in the displacement of the plunger legs a predetermined distance along the longitudinal axes of the chambers.

23. The device of claim 21 wherein the barrel has a third chamber for holding another agent to be added to the composite material and the plunger comprises a third distal leg adapted for slidable entry into the third chamber of the barrel.

24. The device of claim 21 wherein the catheter has a substantially flexible region and a substantially rigid region connected by an adapter.

25. The device of claim 21 further comprising a first and second cartridge loaded with the components, and wherein the first and second chambers are adapted to accommodate the respective first and second cartridges.

26. A kit for the delivery to a situs of multi-component, highly viscous, polymerizable, composite materials, the kit comprising:
- at least a first component and a second component forming, when blended, a multi-component, highly viscous, polymerizable, composite material;
- a barrel having a first and second chamber for holding separately the respective first and second components, the chambers being aligned along a longitudinal axis of the barrel and each having a volume;
- a plunger comprising first and second distal legs adapted for slidable entry into the chambers of the barrel and having a proximal end of the plunger comprising external threads;
- a plunger actuation member having a handle permitting rotation of the plunger actuation member with torque sufficient to express the first and second components and internal threads for cooperation with the external threads of the plunger such that rotation of the plunger actuation member advances the plunger legs into the barrel chambers and displaces the first and second components, the plunger being completely surrounded by the plunger actuation member;
- an attachment mechanism between the barrel and the plunger actuation member, the mechanism further allowing the device to withstand pressures up to about 500 to 2,000 psi;
- a mixing element for receiving the displaced components from the barrel chambers and blending the components substantially homogeneously to form the composite material, the mixing element having a volume; and
- a catheter having a volume and delivering the composite material to the situs, wherein the combined volume of the chambers is greater than the combined volume of the mixing element and the catheter.

27. The device of claim 26 wherein the attachment mechanism includes at least one tongue on the barrel and at least one groove on the plunger actuation member aligned with the at least one tongue for attaching the barrel to the plunger actuation member.

28. The device of claim 26 wherein the catheter has a substantially flexible region and a substantially rigid region connected by an adapter.

29. A kit for the delivery to a situs of multi-component, highly viscous, polymerizable, composite materials, the kit comprising:
- at least a first component and a second component forming, when mixed, a multi-component, highly viscous, polymerizable, composite material;
- a barrel having a first and second chamber for holding separately the respective first and second components, the chambers being aligned along a longitudinal axis of the barrel, and at least one tongue;
- a plunger comprising first and second distal legs adapted for slidable entry into the chambers of the barrel and having a proximal end of the plunger comprising external threads; and
- a plunger actuation member having at least one groove aligned with the at least one tongue for attaching the barrel to the plunger actuation member, a handle permitting rotation of the plunger actuation member with torque sufficient to express the components, and internal threads for cooperation with the external threads of the plunger such that rotation of the plunger actuation member advances the plunger legs into the barrel chambers and displaces the first and second components from the barrel chambers and into a mixture to form the composite material, such cooperation between the internal threads of the plunger actuation member and the external threads of the plunger allowing the device to withstand pressures up to about 500 to 2,000 psi, the plunger being completely surrounded by the plunger actuation member.

* * * * *